US006758834B2

(12) United States Patent
Grooters

(10) Patent No.: US 6,758,834 B2
(45) Date of Patent: *Jul. 6, 2004

(54) AORTIC CANNULA WITH SPOON-SHAPED LIP

(76) Inventor: Ronald K. Grooters, 5535 Glen Oaks Pt., West Des Moines, IA (US) 50266-6627

(*) Notice: Subject to any disclaimer, the term of this patent is extended or adjusted under 35 U.S.C. 154(b) by 65 days.

This patent is subject to a terminal disclaimer.

(21) Appl. No.: 09/726,733

(22) Filed: Nov. 30, 2000

(65) Prior Publication Data

US 2001/0000082 A1 Mar. 29, 2001

Related U.S. Application Data

(60) Division of application No. 09/467,326, filed on Dec. 20, 1999, now Pat. No. 6,186,987, which is a continuation-in-part of application No. 09/221,903, filed on Dec. 28, 1998, now Pat. No. 6,254,578, which is a continuation-in-part of application No. 08/940,745, filed on Sep. 30, 1997, now Pat. No. 5,876,383.

(51) Int. Cl.[7] .......................... A61M 5/00; A61M 25/00
(52) U.S. Cl. ....................................... 604/264; 604/532
(58) Field of Search ................................ 604/264, 239, 604/282, 523, 532, 164.01, 272, 273, 280, 274

(56) References Cited

U.S. PATENT DOCUMENTS

| 191,879 A | | 6/1877 | Pfarre | |
|---|---|---|---|---|
| 1,879,249 A | * | 9/1932 | Honsaker | 604/27 |
| 1,998,225 A | | 4/1935 | Dow | 128/349 |
| 2,458,305 A | * | 1/1949 | Sanders | 604/526 |
| 3,656,486 A | * | 4/1972 | Robertson | 606/108 |
| 3,828,767 A | | 8/1974 | Spiroff | 128/2.05 |
| 4,198,984 A | | 4/1980 | Taylor | 128/349 |
| 4,276,880 A | | 7/1981 | Malmin | 128/221 |
| 4,361,152 A | | 11/1982 | Patel | 604/99 |
| 4,368,738 A | | 1/1983 | Tersteegen et al. | 604/180 |
| 4,617,019 A | | 10/1986 | Fecht et al. | 604/280 |
| 4,643,712 A | | 2/1987 | Kulik et al. | 604/4 |
| 4,795,446 A | | 1/1989 | Fecht | 604/264 |
| 4,863,441 A | | 9/1989 | Lindsay et al. | 604/280 |
| 5,044,369 A | | 9/1991 | Sahota | 604/280 |
| 5,084,033 A | * | 1/1992 | O'Neill et al. | 604/264 |
| 5,147,334 A | | 9/1992 | Moss | 604/264 |
| 5,167,645 A | | 12/1992 | Castillo | 604/272 |
| 5,259,371 A | | 11/1993 | Tonrey | 128/200.26 |
| 5,290,267 A | | 3/1994 | Zimmermann | 604/272 |
| 5,320,599 A | | 6/1994 | Griep et al. | 604/35 |
| 5,344,412 A | | 9/1994 | Wendell et al. | 604/280 |
| 5,354,288 A | | 10/1994 | Cosgrove et al. | 604/264 |

(List continued on next page.)

FOREIGN PATENT DOCUMENTS

| EP | 0092927 B1 | 8/1986 |
|---|---|---|
| EP | 0159773 B1 | 6/1988 |
| EP | 0705617 A1 | 4/1994 |
| EP | 0612536 A1 | 8/1994 |
| WO | WO 96/18428 | 6/1996 |

*Primary Examiner*—Brian L. Casler
*Assistant Examiner*—Matthew DeSanto
(74) *Attorney, Agent, or Firm*—McKee, Voorhees & Sease, P.L.C.

(57) ABSTRACT

An improved aortic cannula is provided for use in heart by-pass surgery. The cannula includes an elongated tube with a terminal end. The terminal end has a ramped surface leading to the discharge opening. The ramped surface terminates in a spoon-shaped lip. The spoon-shaped lip directs blood out of the cannula opening toward the ascending aorta or aortic arch in a U-shaped dispersion so as to preclude impact on the aortic wall. A bead adjacent the opening facilitates dispersion of the exiting blood. The opening has an upper edge with an inverted V-shaped contour which also facilitates dispersion of the blood.

27 Claims, 2 Drawing Sheets

U.S. PATENT DOCUMENTS

| | | | |
|---|---|---|---|
| 5,360,414 A | 11/1994 | Yarger | 604/264 |
| 5,360,416 A * | 11/1994 | Ausherman et al. | 604/158 |
| 5,364,373 A | 11/1994 | Waskonig et al. | 604/272 |
| 5,389,074 A | 2/1995 | Parker et al. | 604/96 |
| 5,407,441 A | 4/1995 | Greenbaum | 604/280 |
| 5,451,216 A | 9/1995 | Quinn | 604/270 |
| 5,456,675 A | 10/1995 | Wolbring et al. | 604/280 |
| 5,480,392 A | 1/1996 | Mous | 604/280 |
| 5,599,322 A | 2/1997 | Quinn | 604/270 |
| 5,616,137 A | 4/1997 | Lindsay | 604/264 |
| 5,643,226 A | 7/1997 | Cosgrove et al. | 604/264 |
| 5,662,619 A * | 9/1997 | Zarate | 604/272 |
| 5,685,865 A * | 11/1997 | Cosgrove et al. | 604/239 |
| 5,749,889 A * | 5/1998 | Bacich et al. | 604/264 |
| 5,873,362 A * | 2/1999 | Parker | 128/207.14 |
| 5,876,383 A | 3/1999 | Grooters et al. | 604/264 |
| 5,976,114 A * | 11/1999 | Jonkman et al. | 604/264 |
| 6,186,987 B1 * | 2/2001 | Grooters | 604/264 |
| 6,254,578 B1 * | 7/2001 | Grooters et al. | 604/264 |

* cited by examiner

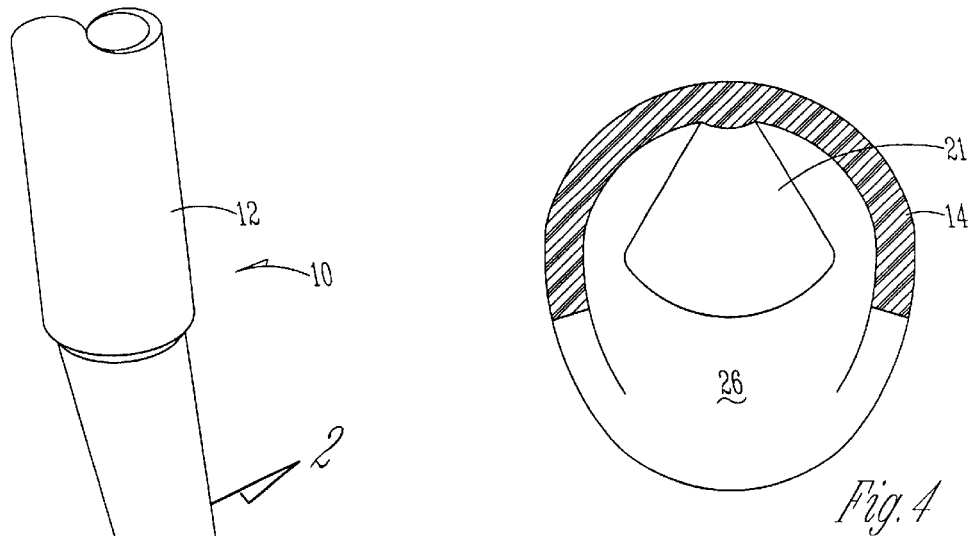
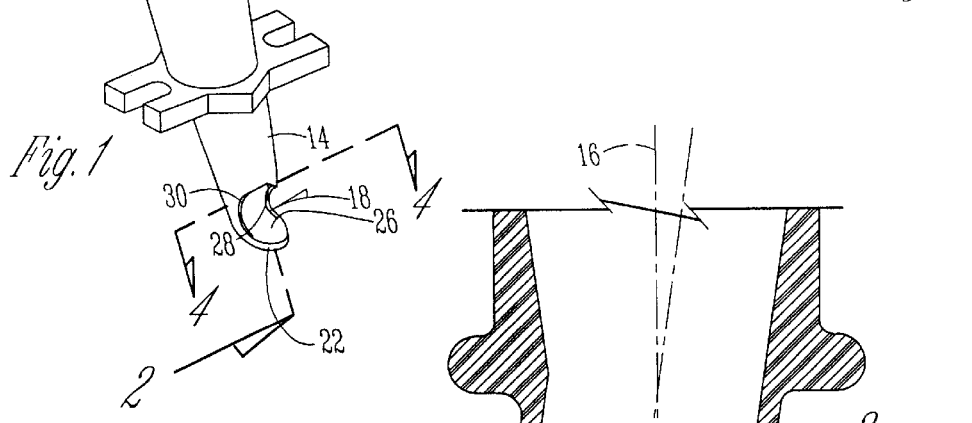
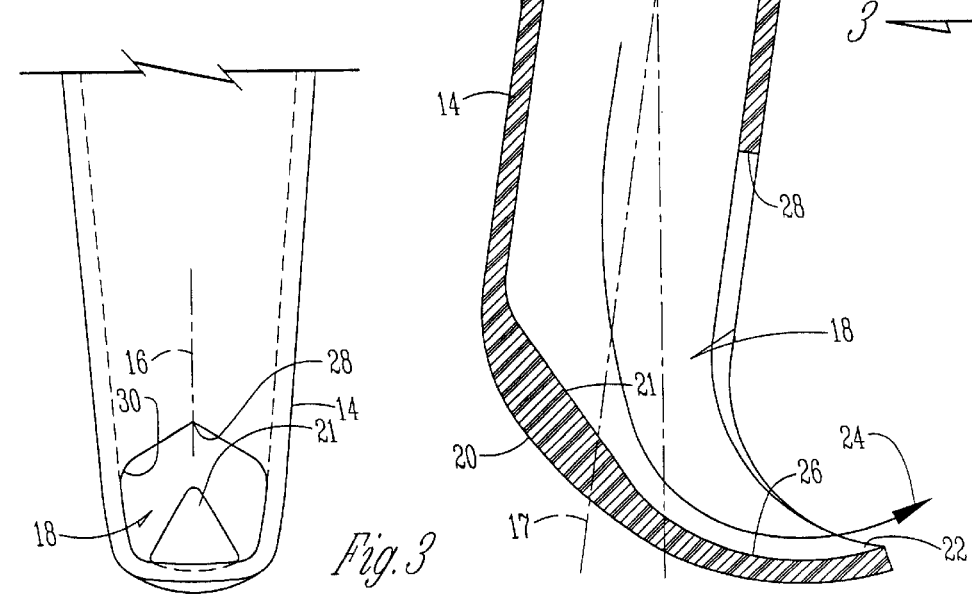

AORTIC CANNULA WITH SPOON-SHAPED LIP

RELATED APPLICATION

This application is a division of application Ser. No. 09/467,326, filed Dec. 20, 1999, now U.S. Pat. No. 6,186,987, which is a continuation-in-part of pending application Ser. No. 09/221,903 filed Dec. 28, 1998 now U.S. Pat. No. 6,254,578, which is a continuation-in-part of application Ser. No. 08/940,745 filed Sep. 30, 1997, now U.S. Pat. No. 5,876,383 issued on Mar. 2, 1999.

BACKGROUND OF THE INVENTION

The present invention relates generally to medical devices and, in particular, aortic cannulas. Aortic cannulas are used to return blood to the aorta while the heart is bypassed during heart surgery. These cannulas are purposely made with small diameters to minimize disruption to the aorta, which in many heart surgery patients have advanced complex atherosclerotic plaque with adherent blood from bithrombi. Some conventional cannulas have a single discharge opening for the blood. It is desirable to eliminate or minimize impact onto the aortic wall of the blood exiting the cannula.

Aortic cannulas generally comprise an elongated tube having a terminal end. In at least some styles of conventional cannulas, a single opening is provided in the terminal end which provides a single stream of blood exiting the cannula and entering the aortic arch. Due to the small diameter of the cannula, the flow velocity of the blood through the single opening in the terminal end of the cannula is extremely high resulting in "jet" flow. The fluid pressure at the discharge end of the prior art cannula is also high. It is believed that the force of this jet stream of blood dislodges atherosclerotic plaque and/or adherent thrombi from the walls of the aorta, causing embolisms and strokes.

Attempts in the art to prevent embolisms resulting from cannulation have included designing the cannula in order to reduce the velocity of blood exiting the terminal end. For instance, U.S. Pat. No. 5,354,288 describes a cannula having a conical diffuser placed toward the proximal end of the cannula. The cannula includes several outlet openings in the sidewall to permit blood deflected by the diffuser to flow out of the cannula. This cannula design, however, still directs blood toward the sides of the aortic arch wherein the atherosclerotic plaque usual lies. Thus, the patient is still susceptible to embolisms and strokes.

Therefore, a primary objective of the present invention is the provision of an improved aortic cannula which disperses blood into the aorta with little, if any, contact on the aortic wall.

Another objective of the present invention is the provision of an improved aortic cannula having a spoon-shaped discharge lip to prevent impact of exiting blood on the aortic wall.

Another objective of the present invention is a provision of an improved aortic cannula which has an internal bead adjacent the terminal end to facilitate blood dispersion from the cannula.

Another objective of the present invention is a cannula which discharges the blood in a U-shaped stream.

Another objective of the present invention is a cannula which discharges the blood in a direction centrally aligned with the aortic lumen so as to avoid or minimize impact on the aortic wall.

A further objective of the present invention is the provision of an improved aortic cannula having a discharge opening with an upper end having an inverted V-shaped contour to facilitate dispersion of blood from the cannula.

These and other objectives will become apparent from the following description of the invention.

SUMMARY OF THE INVENTION

The improved aortic cannula of the present invention includes an elongated tube having a terminal end. The tube has an internal curved surface leading to an enlarged opening adjacent the terminal end of the cannula. In one aspect of the present invention, the curved surface terminates in a spoon-shaped lip extending beyond the perimeter of the tubular cannula, such that the blood exits the spoon-shaped lip of the cannula in a hollowed or U-shaped stream in a direction centrally aligned with the aorta lumen. In another aspect of the present invention, a bead is formed in the tube adjacent the terminal end to facilitate dispersion of blood from the opening. In yet another aspect of the present invention, the opening has an upper edge with an inverted V-shaped contour to further facilitate dispersion of blood from the cannula.

BRIEF DESCRIPTION OF THE DRAWINGS

FIG. 1 is a perspective view of the exemplary improved aortic cannula of the present invention.

FIG. 2 is a sectional view of the terminal end of the aortic cannula shown along lines 2—2 of FIG. 1.

FIG. 3 is an elevation view of the exemplary embodiment of the aortic cannula taken along lines 3—3 of FIG. 2.

FIG. 4 is a sectional view taken along lines 4—4 of FIG. 1 showing an exemplary shape of the bead in the cannula of the present invention.

DETAILED DESCRIPTION OF THE PREFERRED EMBODIMENT

Figure 5:
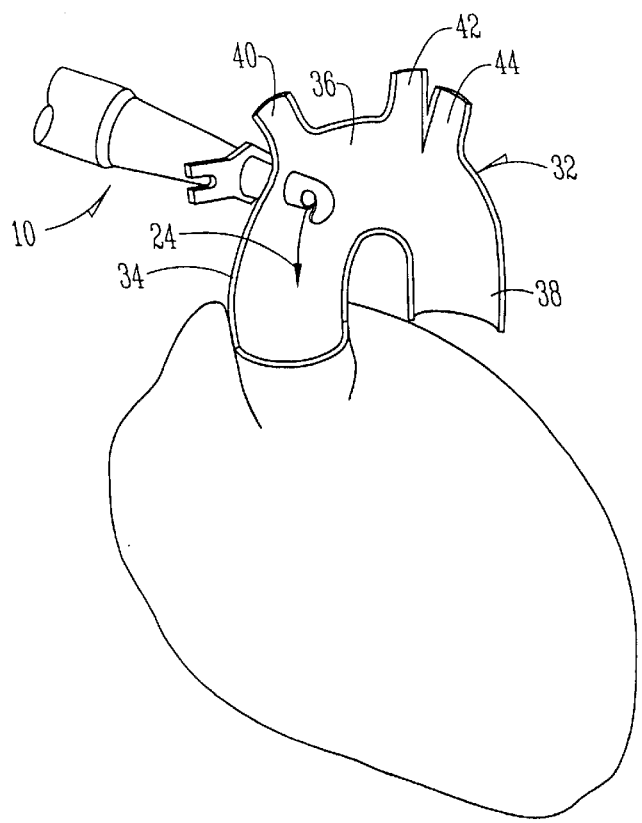
FIG. 5 is a schematic diagram of the heart and its primary blood vessels with the aortic cannula of the present invention inserted into the ascending aorta.

The present invention will be described as it applies to its preferred embodiment. It is not intended that the present invention be limited to the described embodiment. It is intended that the invention cover all alternatives, modifications, and equivalencies which may be included within the spirit and scope of the invention.

An exemplary embodiment of the improved aortic cannula of the present invention is generally designated by the reference numeral 10 in the drawings. With reference to FIGS. 1 and 2, the cannula 10 comprises an elongated tube 12 with a terminal end 14. As best seen in FIG. 2, it is preferred that the terminal end 14 is angled or tilted slightly with respect to the longitudinal axis 16 of the tube 12. Preferably, by way of example and not limitation, the relative angle between the axis 17 of the terminal end 14 and the longitudinal axis 16 of the tube 12 is approximately 5° to 20°. The diameter of the tube 12 may taper toward the terminal end 14.

In one aspect of the present invention, an enlarged opening 18 is provided in the terminal end 14. The opening has a lower end 26 and an upper end 30. The upper edge of the opening 18 is curved, preferably with an inverted V-shape apex 28, as best seen in FIG. 3.

Figure 7:
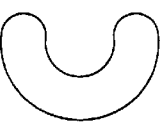
FIG. 7 is a schematic view showing the cross sectional shape of the blood immediately after discharge from the cannula of the present invention.
Figure 8:
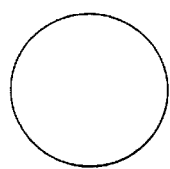
FIG. 8 is a view similar to FIG. 7 showing the jet stream of blood exiting the single opening of a prior art cannula.

In a second aspect of the present invention, the improved cannula has a spoon-shaped lip 22. A curved or ramped surface 20 directs blood along the spoon-shaped lip 22 extending from the terminal end 14. Preferably, the lip 22 extends from the terminal end 14 at approximately 70°–90° relative to the longitudinal axis 16 of the tube 12. It is preferred that the lip 22 extends beyond the perimeter of the tube 12, as best seen in FIG. 2. The spoon-shaped lip 22 preferably includes a side-to-side curvature as well as a front-to-back curvature. The spoon-shaped lip 22 causes the blood to exit the opening 18 in a hollowed stream, such as the U-shaped dispersion shown in FIG. 7, without a wide band broadcast or fan. Thus, the exiting blood does not impact upon the wall of the ascending aorta 34, as shown in FIG. 5, or the aortic arch 36, if used in that direction.

In a further aspect of the present invention, a bead 21 is formed on the ramped surface 20. Preferably, the bead 21 is wedge-shaped and integrally formed with the tube 12. An explanary embodiment is shown in FIG. 4, but other shapes and constructions will be apparent to one skilled in the art, such as a non-integral construction of the bead 21 in the tube 12.

In FIG. 5, the aorta is designated by the reference numeral 32. The aorta 32 includes three main sections, the ascending aorta 34, the transverse aortic arch 36, and the descending aorta 38. The aortic arch 36 is the primary area where atherosclerotic plaque is found in patients needing heart bypass surgery. Branching from the aorta 32 are three large arteries, the innominate artery 40, the left carotid 42, and the left subclavian 44.

The opening 18, ramped surface 20, bead 21 and lip 22 allow the blood to be forced through the cannula 10 at a lower pressure. The large opening also reduces the velocity of the exiting blood. The ramped surface 20 and the lip 22 direct the blood toward the ascending aorta 34, as indicated by arrow 24, at an angle substantially 70°–90° from the longitudinal axis 16 of the tube 12. The blood may alternately be directed toward the aortic arch 36. Without the extended lip 22, which in effect extends the lower edge 26 of the opening 18 beyond the top edge 28 of the opening, the ramped surface 20 alone will only direct the exiting blood at an angle approximately 45° from the longitudinal axis 16 of the tube 12. The blood exits the opening 18 in a narrow hollow stream axially directed in the lumen of the ascending aorta 34 or aortic arch 36, thereby avoiding impact with the wall of the aorta. The bead 21 facilitates dispersion of the blood by interrupting the linear flow path through the tube 12. The inverted V-shaped apex 28 of the opening 18 also permits blood to exit the opening 18 adjacent the upper edge 30 thereof, and mix with the blood passing along the lip 22, thereby facilitating dispersion. The large size of the opening 18 also decreases the velocity of the blood exiting from the cannula 10.

Figure 6:
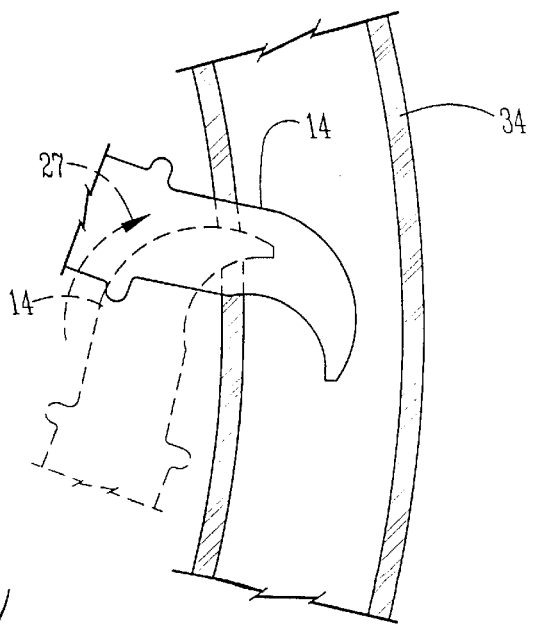
FIG. 6 is a schematic sectional view showing the initial and complete insertion positions of the cannula in the aorta.

After an incision is made by the surgeon in the ascending aorta 34, the cannula 10 is positioned such that the tube 12 is relatively close to the aorta. The end of the lip 22 is inserted into the incision and the cannula 10 is rotated upwardly as indicated by the arrow 27 in FIG. 6, such that the tube 12 extends away from the aorta 32. The lip spreads and opens the incision for quick and easy insertion of the cannula terminal end 14, as seen in FIG. 5. In FIG. 6, the initial insertion position of the lip 22 is shown in broken lines, while the final insertion position of the terminal end 14 is shown in solid lines. This process is reversed for removal of the cannula 10 from the aorta 32.

Thus, the aortic cannula 10 of the present invention is quickly and easily inserted through a minimally sized incision in the aorta 32, thereby reducing risk of damage to the aortic wall and optimizing patient recovery. Potential damage to the wall of the aorta is also reduced since the spoon-shaped lip 22 eliminates or minimizes impact of exiting blood onto the aorta wall. Furthermore, by directing blood flow centrally along the aortic lumen, the improved cannula 10 reduces the chance that the plaque will become dislodged during cardiac bypass surgery, and thus, helps to reduce the risk of embolism and strokes. In prior art cannulas, the blood is directed towards the aortic wall and thus may dislodge plaque, which then can enter the blood stream and cause a stroke.

Whereas the invention has been shown and described in connection with the preferred embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. An aortic cannula comprising:
   an elongated tube having a longitudinal axis and a terminal end with an opening therein, wherein the opening has an upper end with an inverted V-shaped contour,
   a lip extending at an obtuse angle from the terminal end adjacent the opening so as to define an outer radius; and
   a raised bead in the outer radius of the tube adjacent the terminal end to facilitate dispersion of blood from the opening.

2. The cannula of claim 1 wherein the lip is spoon-shaped.

3. The cannula of claim 1 wherein the lip is concave.

4. The cannula of claim 1 wherein the lip extends approximately 70°–90° relative to the longitudinal axis.

5. The cannula of claim 1 wherein the lip extends beyond the perimeter of the tube.

6. The cannula of claim 1 wherein the opening is disposed on the tube to direct blood toward the center of the aorta.

7. The cannula of claim 1 wherein the bead is wedge shaped with a narrow upstream end and a wide downstream end.

8. The cannula of claim 1 wherein the bead is located in the tube opposite the opening.

9. The cannula of claim 1 wherein the tube has inner and outer walls, and the bead is on the inner wall.

10. The cannula of claim 1 wherein the opening is pentagonally shaped.

11. An aortic cannula comprising:
    an elongated tube having a longitudinal axis and a terminal end with an opening therein;
    a lip extending at an obtuse angle from the terminal end adjacent the opening so as to define an outer radius; and
    a raised bead in the outer radius of the tube adjacent the terminal end to facilitate dispersion of blood from the opening, wherein the bead is located in the tube opposite the opening.

12. The cannula of claim 11 wherein the lip is spoon-shaped.

13. The cannula of claim 11 wherein the lip is concave.

14. The cannula of claim 11 wherein the lip extends approximately 70°–90° relative to the longitudinal axis.

15. The cannula of claim 11 wherein the lip extends beyond the perimeter of the tube.

16. The cannula of claim 11 wherein the opening is disposed on the tube to direct blood toward the center of the aorta.

17. The cannula of claim 11 wherein the bead is wedge shaped with a narrow upstream end and a wide downstream end.

18. The cannula of claim 11 wherein the tube has inner and outer walls, and the bead is on the inner wall.

19. The cannula of claim 11 wherein the opening is pentagonally shaped.

20. An aortic cannula comprising:

an elongated tube having a longitudinal axis and a terminal end with an opening therein, wherein the tube has inner and outer walls;

a lip extending at an obtuse angle from the terminal end adjacent the opening so as to define an outer radius; and a raised bead in the outer radius of the tube adjacent the terminal end to facilitate dispersion of blood from the opening, wherein the bead is on the inner wall.

21. The cannula of claim 20 wherein the lip is spoon-shaped.

22. The cannula of claim 20 wherein the lip is concave.

23. The cannula of claim 20 wherein the lip extends approximately 70°–90° relative to the longitudinal axis.

24. The cannula of claim 20 wherein the lip extends beyond the perimeter of the tube.

25. The cannula of claim 20 wherein the opening is disposed on the tube to direct blood toward the center of the aorta.

26. The cannula of claim 20 wherein the bead is wedge shaped with a narrow upstream end and a wide downstream end.

27. The cannula of claim 20 wherein the opening is pentagonally shaped.

\* \* \* \* \*